United States Patent
Fox

(10) Patent No.: US 7,173,256 B2
(45) Date of Patent: Feb. 6, 2007

(54) FLUORESCENT IMAGE CALIBRATION STEP WEDGE, AND USE THEREOF IN ILLUMINATION FOR FLUORESCENT IMAGING AND AUTOMATIC EXPOSURE

(76) Inventor: John S. Fox, 684 Poinsettia Park South, Encinitas, CA (US) 92024

( * ) Notice: Subject to any disclaimer, the term of this patent is extended or adjusted under 35 U.S.C. 154(b) by 382 days.

(21) Appl. No.: 10/810,993

(22) Filed: Mar. 26, 2004

(65) Prior Publication Data

US 2005/0211912 A1   Sep. 29, 2005

(51) Int. Cl.
   *G01N 21/64* (2006.01)
(52) U.S. Cl. .................................... 250/458.1
(58) Field of Classification Search ............. 250/458.1
   See application file for complete search history.

(56) References Cited

U.S. PATENT DOCUMENTS

| | | | |
|---|---|---|---|
| 6,369,928 B1* | 4/2002 | Mandella et al. | 359/204 |
| 6,379,622 B1* | 4/2002 | Polak et al. | 422/82.06 |
| 6,414,779 B1* | 7/2002 | Mandella et al. | 359/212 |
| 6,459,805 B1* | 10/2002 | Reynolds et al. | 382/128 |
| 2005/0176056 A1* | 8/2005 | Sammak et al. | 435/6 |

* cited by examiner

*Primary Examiner*—David Porta
*Assistant Examiner*—Mark R. Gaworecki
(74) *Attorney, Agent, or Firm*—Fuess & Davidenas

(57) ABSTRACT

Both intensity(ies) and color(s) of fluorescent emissions appearing within a well-balanced multi-color fluorescent composite image, normally made simultaneously along each of multiple axis of a macroscopic specimen such as a mouse, are calibrated. The image is so calibrated in all its multiple intensity-adjusted fluorescent colors as may variously appear in any and all of the image's regions by one or more planar elements each having different regions variably fluorescing at predetermined intensities and, optionally also, at multiple different colors. The resulting panoramic composite image of a fluorescing, and multiply-fluorescing, specimen in which image these calibration elements also appear contains a great deal of calibration information, optionally showing scales in any of dimension, overall brightness, color temperature and/or the separate emission intensities of, permissively, each of several separate differently-colored fluorescent lights.

13 Claims, 3 Drawing Sheets

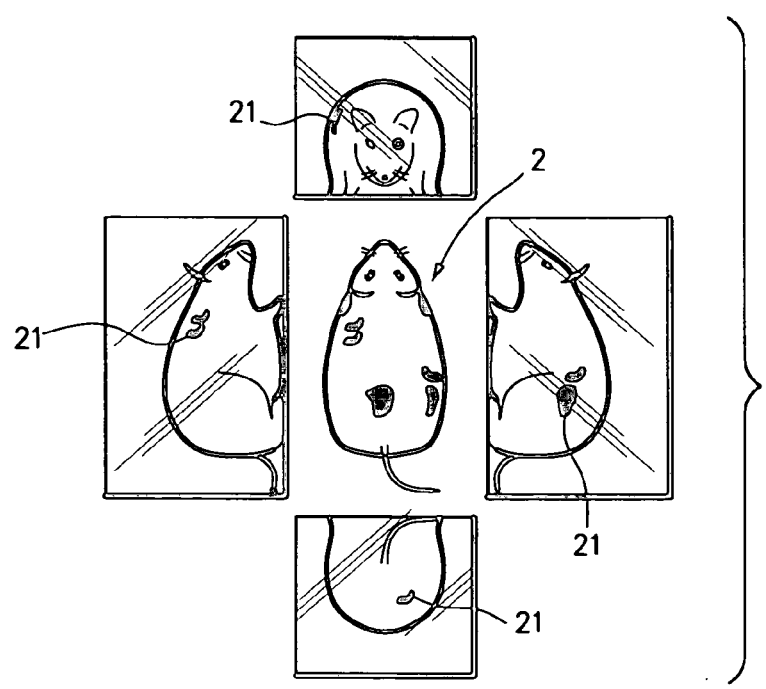
FIG. 2
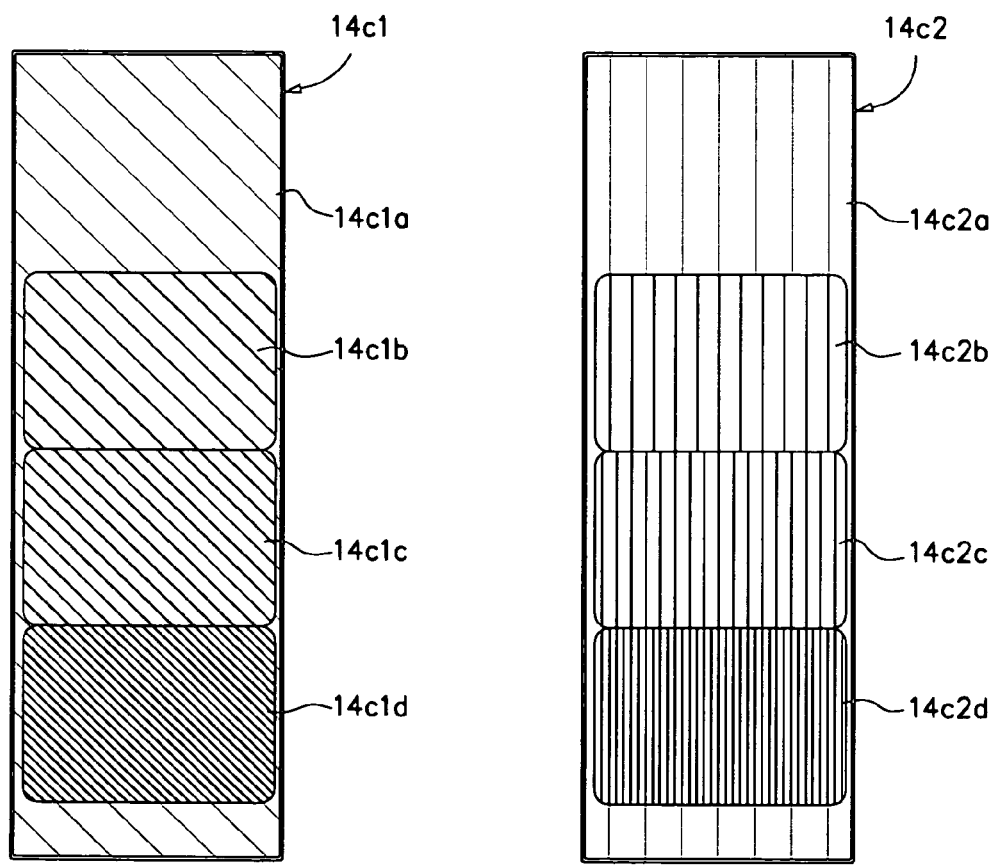
FIG. 4a
FIG. 4b

FLUORESCENT IMAGE CALIBRATION STEP WEDGE, AND USE THEREOF IN ILLUMINATION FOR FLUORESCENT IMAGING AND AUTOMATIC EXPOSURE

REFERENCE TO RELATED PATENT APPLICATIONS

The present patent application is related to U.S. patent application Ser. No. 10/788.724 for CONTROLLED-INTENSITY MULTIPLE-FREQUENCY MULTIPLE-AXIS ILLUMINATION OF MACROSCOPIC SPECIMENS FROM A SINGLE LIGHT SOURCE USING SPECIAL BIFURCATED CABLES. The present patent application is also related to U.S. patent application Ser. No. 10/775,792 for ILLUMINATING AND PANORAMICALLY VIEWING A MACROSCOPICALLY-SIZED SPECIMEN ALONG A SINGLE VIEWING AXIS AT A SINGLE TIME. Both related patent applications are to the selfsame John Fox who is the inventor of the present application. The contents of the related patent applications are incorporated herein by reference.

BACKGROUND OF THE INVENTION

1. Field of the Invention

The present invention generally concerns (1) fluorescent calibration elements generally, but not exclusively, usable with (2) an apparatus, as are commonly but not exclusively used in laboratories, for illuminating and for viewing a macroscopically-sized specimen, for example a mouse, including and most commonly (3) along each of potentially multiple viewing axis. The present invention also generally concerns the methods of locating and using such (1) fluorescent calibration elements.

The present invention particularly concerns the positioning and use of one or more fluorescent calibration elements during any of the illuminating, viewing and or recording of the image of a macroscopically-sized specimen, such as a mouse. The illuminations are potentially along each of multiple viewing axis at a single time, and each such illumination of the specimen along each such axis may be in, potentially, multiple colors (i.e., wavelengths, or frequencies) as serve to excite corresponding fluorescent emissions in the specimen in each of multiple colors (i.e., wavelengths, or frequencies). Moreover, each of the potentially plural induced fluorescent emissions (along each illumination and viewing axis) may be independently controlled in intensity. In particular, multiple fluorescing colored fields as appear within a composite, panoramic, image of the specimen may be—by the adjustability of the fluorescent emissions—both (1) made clearly visible, and (2) balanced one color and area of fluorescent emission to the next—meaning that a bright field of one fluorescent color will not "swamp" a dimmer fluorescent field of another color. Moreover, and nonetheless that the induced fluorescent emissions may be adjusted in intensity—meaning that the dim may be made bright simultaneously that the bright may be made dim—the true and actual intensity of each fluorescent emission may be quantitatively known.

The present invention will be seen to still further concern that all such variable illumination along each of multiple axis as produces multi-color fluorescent emissions of controlled intensity (along each axis, as are individually visible in a composite image) is efficiently realized.

Accordingly, whereas (1) a first related invention regarding panoramic viewing may be simplistically regarded as showing how to comprehensively illuminate and view a macroscopic specimen along a single axis at a single time, and (2) a second invention regarding a fluorescent image calibration step wedge may be simplistically regarded as showing how to quantify each of multiply-colored fluorescent emissions permissively simultaneously appearing in each of multiple (illumination and) viewing axis in a composite, panoramic, image, (3) the present invention shows how efficiently illuminate a macroscopic specimen, permissively along each of multiple axis, with some sophistication to the end to that each of multiple fluorescent emissions induced in the specimen (by the illuminating) will be well and easily viewable. Specifically, the present invention will be seen to regard image illumination for viewing where such illumination is not only realized along each of multiple viewing axis at a single time, but where this axial illumination is readily selectively balanced in either of intensity (and/or, less commonly, color (i.e., wavelength, or frequency)). This selective balancing of illuminations—permissively separately independently along each of a plurality of specimen illumination paths—is so that fluorescence induced in the specimen and appearing in the composite image as different fields having more than one color (i.e., wavelengths, or frequencies) will so appear with roughly equal intensity each color.

Despite this "adjustment" in the intensities of each fluorescent color, the real and true intensity of fluorescence at each color (i.e., wavelength, or frequency), is readily calibrated for each color, and is even so calibratable separately along each illumination path.

2. Description of the Prior Art

2.1 General Laboratory Apparatus and Methods for Illumination and Observation of Macroscopically Sized Specimens Apparatus to illuminate and to hold macroscopically-sized specimens for viewing, including viewing as may involve the taking of photographs, are known in the art. These apparatus hold secure a macroscopically-sized specimen to be viewed, including for example a live specimen and more particularly a laboratory animal and still more particularly a mouse, upon a specimen stage. A source of illuminating radiation—most commonly a narrowband, colored, light radiation—is brought to bear upon the held specimen.

The illuminating radiation sources may consist of the emitting end of a fiber optic, a fiber optic bundle, or a light pipe or the like. The illuminating radiation itself may, by way of example, be sufficient so as to induce fluorescence in the specimen, including in a specimen as may have been previously fused with fluorescing agents that most commonly serve to make regions of the specimen that are of interest more visible or otherwise detectable.

The illuminated specimen may be, and commonly is, digitally imaged, but may also and/or alternatively be photographed, including in its emitted fluorescent light.

2.2 The Utility of Introducing Quantitative Rigor into Observations of Macroscopically Sized Specimens The present and related inventions will generally be seen to be directed to a common goal of imparting the imaging, and photographing, of macroscopic specimens (especially specimens as are caused to fluoresce)—a process generally presently conducted "ad hoc"—with a great deal of scientific rigor.

As of present, circa 2004, the images, or photographs produced by conventional illumination and observation of macroscopically-sized specimens, such as the biological specimen of a mouse, tend to be rather crude. Most typically the mouse will be illuminated so that an region of interest, such as a tumor, previously absorbing fluorescent dye will be caused to fluoresce, and the fluorescent region of the resulting image is indicated only that the mouse has the tumor.

In this rudimentary observation many, many things are lacking.

First, it is not possible to view the mouse specimen along multiple axis, or panoramically around a broad angular field, at the same time. This precludes looking at the same tumor in the mouse from two or more different directions, and from looking at multiple tumors as may exist within different regions of the mouse all at the same time.

Accordingly, it would firstly be useful if a single macroscopically-sized specimen, for example a mouse, could be observed along each of multiple axis, for example left side and right side and fore and aft, all at the same time.

Second, no dimensional scale, either linear or grid, typically accompanies the viewed image of the specimen (the mouse). Such a scale is useful for, by way of example, judging the dimension(s) and volume of the observed tumor. Accordingly, it would secondly be useful if the image of a specimen (for example, a mouse) inherently contained a scale of either the linear or the grid type.

Third, the illumination is commonly so as to induced fluorescence of a single fluorescing agent at a single color at a single time. Even though a resulting image of specimen, which is normally preserved as a photograph, may be in color, for example of a green fluorescing region within a white mouth, the image, and photograph, really contains no more information than a black and white photograph. This simplistic observation obviates the possibility that a single specimen should contain multiple fluorescing agents which fluoresce at different colors so as to identify corresponding regions of interest within the (single) specimen. This simplistic observation does not make optimal use of modern color digital cameras.

Although multi-color photographs of multiple fluorescent colors within a single specimen may in the past have been made, any such images would likely have been derived by illumination with a single light sufficient so as to induce emission in each of multiple fluorescent agents. Otherwise the "plumbing" of excitation lights to the specimen may become unwieldy. To the best knowledge of the inventor, it has not been commonly thought to simultaneously illuminate a macroscopic specimen with multiple colors (as are targeted to induce associated multiple fluorescent emissions), let alone to attempt adjustment of the intensity of each color within a resulting composite image.

In other words, a body impregnated with fluorescent red dye may appear to fluoresce red light quite brightly while another body (or the same body or portion thereof as may have picked up green fluorescent dye at a different time and/or to a different extent) may, under the same common illumination, fluoresce green light quite dimly. Nonetheless that the body, or tumor, fluorescing red shows brightly in the image, and the body, or tumor, fluorescing green shows but dimly in the image, the "green" tumor or stage may be of equal size and/or interest to the "red" tumor. What looks bright, and what looks dim, in the composite image is, of course, a function of the efficiency of the uptake of the fluorescent dyes, the efficiency of the illumination excitation of each, and the efficiency of each dye to fluoresce, among other factors. Thus, even should multiple illumination sources of different frequencies be simultaneously "optically plumbed" to illuminate the macroscopic body under observation, independently adjusting selecting illumination frequencies and adjusting the intensity of each so that the resulting "red" tumor and "green" tumor images in the composite are somewhat comparable.

Accordingly, it would thirdly be useful if each of multiple regions fluorescing at different colors within a single composite image of a specimen (for example, a mouse) could be independently adjusted in intensity, clearly rendering visible in the composite image those things and/or regions that the researcher and image taker desires to be well seen, while suppressing within the composite image other things and/or regions that are deemed unimportant. It would be especially useful if this selective differential "highlighting" of each of multiple colors of fluorescent emission could somehow be realized from but a single, common, illuminating light source.

Some little thought will reveal, however, that should such control be given to the image maker, then it may soon become impossible to know what has been done in manipulation of the composite image and its colors, and to know what imaged things and/or regions "really" look like under normal conditions. It thus, fourth, problematic that no scale of the intensity(ies) of (potentially several different) fluorescent emission(s) typically accompanies the viewed image of the specimen (the mouse). Such a scale is useful for, by way of example, judging how bright or how dim were things and/or regions—nonetheless to their appearance within the composite image—under normal, and standard, illumination conditions.

Accordingly, it would fourthly be useful if the image of a specimen (for example, a mouse) inherently contained a scale of by which any of the intensity(ies), color(s), or, as even more exotic criteria seldom useful, radiation temperature. The color scale might be broken down into hue, chroma (purity, or saturation) and brightness (value). In this manner a viewer of a composite image might be able to say: "I see by comparison to a scale that is within the selfsame image that this clearly visible first object (or area) fluoresced red, and that it was in fact quite bright, even to the point of obscuration, until intentionally diminished in intensity. Meanwhile I also see by comparison to another portion of the same scale, or another scale also contained within the image, that this equally clearly visible second object (or area) fluoresced green, but only dimly so, and that this second object has intentionally been accentuated in intensity by action of the image maker."

2.3 Definitions of "Optical Density" and "Optical Transmittance"

The fluorescent calibration step wedge of the present invention will be seen to vary in optical density (OD) and optical transmittance (T).

By definition, optical density (OD) is, for a given wavelength, an expression of the transmittance of an optical element. Optical density is expressed by log 10(1/T) where T is transmittance. The higher the optical density, the lower the transmittance. Optical density times 10 is equal to transmission loss expressed in decibels, e.g., an optical density of 0.3 corresponds to a transmission loss of 3 dB.

Also by definition, transmittance is the ratio of the transmitted power to the incident power. In optics, transmittance is usually expressed as optical density or in percent. Transmittance was formerly called "transmission."

2.4 Quantum Dots

The fluorescent calibration step wedge of the present invention will also be seen to optionally employ quantum dots.

The following abbreviated explanation of quantum dots is in accordance with the paper "Probing the Optical Properties of Single Quantum Dots" by Jeffrey R. Krogmeier, Jeeseong Hwang, & Lori S. Goldner, National Institute of Standards and Technology, Optical Technology Division, Physics Laboratory, 100 Bureau Drive, Mail Stop 8441, Gaithersburg, Md. 20899 USA Semiconductor nanocrystals or quantum dots are gaining interest as fluorescent tags for biological molecules due to their large quantum yield and photostability. Quantum dots are semiconductor crystallites 2 nm to 10 nm in diameter that contain approximately 500–1000 atoms of materials as cadmium and selenide. Quantum dots fluoresce with a broad absorption spectrum and a narrow emission spectrum. The larger the quantum dot the longer wavelength emitted. The broad absorption spectrum allows many different quantum dots to be excited with one excitation source. The emission spectra for each dot is typically very narrow, on the order of 30 nanometers, which permits spectral resolution of adjacent dots.

Quantum dots are sometimes employed as biological tags. In order to employ quantum dots as biological tags, the nanocrystal must be water soluble and capable of being conjugated to the biological molecule of interest. To accomplish this, much effort has been dedicated to functionalizing the nanocrystal surface with water-soluble, reactive chemical moieties. To employ quantum dots in biological assays, the optical properties of functionalized quantum dots must be understood. In the approach of the subject paper, single molecule confocal microscopy is used to probe the fluorescent properties of functionalized quantum dots at the single particle level. Others have shown that unfunctionalized or bare quantum dots demonstrate fluorescence intermittency or blinking on the millisecond timescale. Carboxylated, amine activated, and bare quantum dots are all useful in understanding the effect of quantum dot coatings on the optical properties.

SUMMARY OF THE INVENTION

The present and related inventions generally contemplate imparting scientific rigor to the imaging, and photographing, of macroscopic specimens, especially such specimens as are caused to fluoresce, and to fluoresce in multiple colors. In accordance with related inventions this composite, multi-colored image of the specimen may be along multiple axis, or even panoramic.

In accordance with the particular present invention a special element called a "fluorescent calibration step wedge" is generally, but not exclusively, usable with such an imaging apparatus, and in the imaging process. The structure of the most preferred embodiment of such a "fluorescent calibration step wedge", or each of them, is relatively simple, being most preferably a number of variably overlapping layers of a fluorescent chemical deposited upon a transparent substrate where the different thicknesses of fluorescent chemical thus obtained will be seen to fluoresce at different intensities under illumination by a light source capable of inducing such fluorescent. Namely, areas of relatively greater deposition of fluorescent chemicals will fluoresce relatively brighter and more intensely while areas of relatively lesser deposition of fluorescent chemicals will fluoresce relatively less brightly and less intensely. This will be true under any radiation (light) source—bright or dim—inducing such fluorescence. The (1) amount of chemical causing each different amount of fluorescent light emission, and (2) the amount of such emission that will be induced under a radiation (light) source, or various radiation (light) sources, of predetermined intensity, is known. Accordingly, if both (1) an area of un-quantified fluorescent emission appears in an image of an object—such as the imaged area of a tumor within a specimen mouse which tumor has been dyed with a fluorescent dye—and (2) an image of the "fluorescent calibration step wedge", appear within the same image at the same time, then the absolute, quantifiable, intensity of the fluorescent light emission from the imaged object (i.e., the mouse tumor) may be determined by comparison to the "fluorescent calibration step wedge". This is true whether or not the illuminating light source (among other factors) is itself relatively brighter or relatively dimmer—as serves to cause both the fluorescent light emission from the imaged object (i.e., the mouse tumor) and from the "fluorescent calibration step wedge" to respectively be relatively brighter or relatively dimmer.

Despite this relatively simple construction, the "fluorescent calibration step wedge" is deployed and used during fluorescent imaging (particularly of macroscopic specimens) in a relatively sophisticated manner. Namely, there can be, and commonly is, used not one single "fluorescent calibration step wedge" for the entire image, but rather a separate "fluorescent calibration step wedge", and more commonly one suitable to each of multiple colors of induced fluorescence, is used for each portion, or part, of a multi-part composite image. Moreover, the intensity of the illuminating radiation (light) as induces fluorescent emission(s) (for example, green and red) in the object under observation (for example, the tumor(s) of the mouse) as is most typically visible in multiple parts of the composite image is separately and independently adjustable. This intensity of the illuminating radiation (light) is so adjusted, including automatically, to the purpose of deriving a good and accurately observable induced fluorescent emission (analogous to "exposure") in each part and portion, and at each color, of a composite multi-color image.

The net results of the sophisticated imaging, and the multiple fluorescent calibration step wedges, may best be explained by example. An investigator, or scientist, may cause to be formed an image—whether photographic or digital it matters not—of a fluorescent, and multiply-fluorescent specimen—such as a tumorous mouse—so that such image might be clearly observed in all regions. The exemplary composite image might show, by way of example, green and red emissive areas (as may represent, for example, different biological properties of the tumor as are differently stained with different fluorescent dyes, or the same property differently stained at different times) on the right side of the mouse and of the composite image, and maybe only a green emissive area, maybe associated with another organ of the mouse, on the left side of the mouse and of the composite image. Now, nonetheless to all areas in all regions showing clearly within the composite image, it may well be, and often is, the case that the individual fluorescent emissions were of vastly different real intensity. For example, in the green and red left side image of the mouse, the red fluorescent light emissions may have been of much less intrinsic brightness than the green fluorescent light emissions, and these colored emissions of two colors are only made to appear commensurate within the composite image because the radiation (light) inducing the (dimmer) red fluorescent emissions at the mouse's left side was copious, while the different radiation (light) inducing the (brighter) green fluorescent emissions at the mouse's same left side was sparse. Meanwhile, the only applicable radiation (light) as serves to induce the only visible fluorescent emission (the green emission) on the right side of the mouse may have had to have been greatly elevated so as to "tease" this nearly invisible (green) fluorescence into visibility.

Now the importance to a biological investigator of the fluorescing, and the greatly variably fluorescing areas of the composite image of the mouse is not in accordance with the intrinsic brightness of these various areas. In simple terms, and by way of the continuing example, it may be very important to note that the (intrinsically dim) green fluorescent area on the right side of the mouse is associated with a different organ of the mouse than that (those) organ(s) imaged at the mouse's left side. This is why the image is desirably, and is, "clearly observable in all regions".

Into this environment of nicely visible, but confusingly related, variously colored fluorescent image areas of a multi-colored fluorescent composite image comes now the "fluorescent calibration step wedge". Several of these "wedges" as besuit all induced fluorescent colors, and as will appear in each part and portion, of the composite image, are used. When the observer of the composite image wants to interpret the absolute, and quantitative, level of fluorescent emission (of any color) appearing at any region of the composite image, then he/she simply makes reference to the appropriately colored step wedge as appears within the same region of the composite image. To continue with the example, the investigator/observer of the composite image may say: "The biological maker regarding which the color green is associated was prominent at the left side of the mouse, where, by comparison to the a green fluorescent step wedge appearing in the same left side of the composite image, this green color may be interpreted to have fluoresced intrinsically very brightly. However, I also see that the biological maker regarding which the color red is associated was also present at the left side of the mouse, where, by comparison to the a red fluorescent step wedge also appearing in the same left side of the composite image, this red color may be interpreted to have fluoresced intrinsically only but dimly. Then, moving to the right side of the image, I again see that the biological maker regarding which the color green is now again present at the right side of the but, where, by comparison to the another green fluorescent step wedge also appearing in the same right side of the composite image, this green color may be interpreted to have fluoresced intrinsically only but dimly.

The "fluorescent calibration step wedges", and each of them, thus permit quantitative determination of sophisticated composite images, particularly in multi-ply illuminated macroscopic specimens, in all fluorescing colors, and in all image regions.

2. Relation of the Present Invention to the Invention of the Related Patent Applications In the related inventions a macroscopically-sized specimen is illuminated along each of multiple axis with radiations of selectable intensities and frequencies so as to support viewing, normally of multiple colors of induced fluorescence, along a single viewing axis. A stage supports specimen to be observed. First and second illumination sources provide respective first and second radiations at selectively predetermined intensities and frequencies. The special "bifurcated" fiber optic cable receives the first radiation into a first one of at least two input ends, and the second radiation into a second one of the at least two input ends, and produces at each of at least two output ends illuminating beams in which both the first and the second radiations are present.

The intensities, and optionally also the frequencies (colors) of these illuminating radiations are controllable so that excitation of multiple different fluorescent agents, and differently fluorescing regions, within a biological specimen such as, by way of example, a tumorous mouse, may be well balanced, with fluorescence of all colors clearly visible.

In the first related patent application for ILLUMINATING AND PANORAMICALLY VIEWING A MACROSCOPICALLY-SIZED SPECIMEN ALONG A SINGLE VIEWING AXIS AT A SINGLE TIME, simultaneous illumination along each of multiple axis for panoramic viewing of a macroscopically-sized specimen such as a mouse along a single viewing axis is realized by use of dichroic mirrors. The selective control of the illumination intensity and/or color(s) of, permissively, each of multiple illuminating lights along each of multiple illumination axis permits that different regions and phenomena, such as tumors, of the specimen as are induced to fluoresce at corresponding different colors and intensities will all appear clearly visible, and well balanced, in a composite image nonetheless to intrinsically being of greatly differing brightness.

In a second related patent application for CONTROLLED-INTENSITY MULTIPLE-FREQUENCY MULTIPLE-AXIS ILLUMINATION OF MACROSCOPIC SPECIMENS FROM A SINGLE LIGHT SOURCE USING SPECIAL BIFURCATED CABLES the macroscopically-sized specimen illuminated with radiations of selectable multiple intensities and frequencies along each of multiple illumination axis for viewing along a single viewing axis is so illuminated by use of special "bifurcated" fiber optic cables. A stage supports specimen to be observed. First and second illumination sources provide respective first and second radiations at predetermined different colors, permissively of different intensities. A special "bifurcated" fiber optic cable receives the first radiation into a first one of two radiation-receiving, or input, ends, and the second radiation into a second one of two radiation-receiving, or input, ends, so as to produce at each of at least two radiation-emitting, or output, ends an illuminating beam in which the first and the second radiations are mixed. The intensities and colors of both radiations are controllable. The multi-color controlled-intensity radiation beams are particularly useful for excitation of multiple different fluorescent agents, and differently fluorescing regions, within a biological specimen such as, by way of example, a tumorous mouse.

To these inventions the present invention adds quantitative rigor to the composite images so produced. Namely, the special "fluorescent calibration step wedge" elements of the present invention, and each of them, will permit, when properly positioned and used during the formation of multi-axis multi-color composite fluorescent images, that the absolute intensity (and also color purity, hue, and/or chroma although variation(s) therein is (are) uncommon) may be rigorously known.

4. A Calibration Element for use with an Apparatus for Illuminating a Macroscopically-sized Specimen Therefor, in one of its aspects the present invention is embodied in an element suitably used in, and with, an apparatus for illuminating a macroscopically-sized specimen for observation along a viewing axis with radiation of multiple colors (i.e., wavelengths, or frequencies) so as to induce multiple, and multiply-colored, fluorescent emissions from the specimen.

In its most preferred embodiment the element includes a body having a plurality of regions that fluoresce under illumination to a corresponding plurality of fluorescent light emission intensities, certain regions appearing to fluoresce relatively more brightly while other regions appear to fluoresce relatively less brightly.

This body comprises preferably consists of a substantially planar substrate, at least one fluorescent substance within the substrate, and one or more coatings applied to different effect in the plurality of areas of the substrate. The coatings are applied so that the different ones of these plurality of substrate regions will, upon exposure to radiation sufficient to induce fluorescent emissions of the fluorescent substance, appear to fluoresce relatively more brightly while other regions will appear to fluoresce relatively less brightly.

Normally, and preferably, the same coating is applied at various thickness to different ones of the plurality of areas of the fluorescent-substance-containing substrate. Thereby relatively less thickly coated regions of the fluorescent-substance-containing substrate will, upon exposure to radiation sufficient to induce fluorescent emissions of the fluorescent substance, appear to fluoresce relatively more brightly. Meanwhile relatively more thickly coated regions of the fluorescent-substance-containing substrate will, upon exposure to the same radiation sufficient to induce fluorescent emissions of the fluorescent substance, appear to fluoresce relatively less brightly.

The substantially planar substrate is preferably made of glass or of plastic.

The fluorescent substance that is within, or upon, the substrate is preferably a fluorescent chemical, or quantum dots.

The at least one substrate coating preferably consists of nickel chrome.

Normally this is the sole and only coating applied; the nickel chrome being applied in various regions to the substrate at the variable extent by dint of being applied to the substrate in multiple regions at a first time, and then re-applied to less than all of the multiple regions upon at least one more, second, time. By this application the coating is more abundant in those of the multiple regions whereat it has been applied at least two times than any regions whereat it has been applied but one time.

The coating—preferably nickel chrome—is so applied to various regions to the substrate at the variable extent by dint of being applied and re-applied to the substrate in multiple regions each region for a variable number of times. Thus accumulations of the coating will be greatest in those regions of the substrate whereat the coating has been applied multiple times.

5. Calibration of an Image Formed in and by an Apparatus for Illuminating a Macroscopically-sized Specimen for Observation Along a Viewing Axis In another of its aspects the present invention is embodied in an apparatus in which an image, at least partially in fluorescent light, of a macroscopically-sized specimen, which image is formed along each of multiple axis, is calibrated in the intensity(ies) and/or color(s) of fluorescent regions appearing within the image.

The calibrated apparatus so functioning for illuminating a macroscopically-sized specimen for imaging and observation along a viewing axis includes a stage for supporting a specimen to be observed; a first illumination source of first radiation of a first color; a second illumination source of second radiation of a second color, different from the first color; and an element for calibrating fluorescent light emissions induced by each of the first and the second radiations. This element has a body having a plurality of regions that fluoresce under illumination to a corresponding plurality of fluorescent light emission intensities, certain regions appearing to fluoresce relatively more brightly while other regions appear to fluoresce relatively less brightly.

The element preferably a substantially planar substrate, and at least two fluorescent chemicals, each primarily responsive to a different one of the first radiation and the second radiation, each applied to a variable extent in various different regions of the substrate so that, upon exposure to the first radiation and to the second radiation sufficient to induce fluorescent emissions from these at least two fluorescent chemicals, areas of the substrate with relatively more chemicals will fluoresce relatively more brightly while areas of relatively less chemical will fluoresce relatively less brightly.

The apparatus may optionally further include a first sensor sensing induced fluorescent radiation emission from a region of the element that is responsive to the first radiation to fluoresce so as to produce a first signal; and a first control circuit, responsive to the first signal, for controlling the first radiation output of the radiation source so that this radiation output is relatively greater when the induced fluorescent radiation emission of the element is sensed by the first sensor to be relatively less, and is relatively lesser when the induced fluorescent radiation emission of element is sensed by the first sensor to be relatively greater.

The apparatus may still further optionally further include a second sensor sensing induced fluorescent radiation emission from a region of the element that is responsive to the second radiation to fluoresce so as to produce a second signal; and a second control circuit, responsive to the second signal, for controlling the second radiation output of the radiation source so that this radiation output is relatively greater when the induced fluorescent radiation emission of the element is sensed by the second sensor to be relatively less, and is relatively lesser when the induced fluorescent radiation emission of element is sensed by the second sensor to be relatively greater.

These and other aspects and attributes of the present invention will become increasingly clear upon reference to the following drawings and accompanying specification.

BRIEF DESCRIPTION OF THE DRAWINGS

Referring particularly to the drawings for the purpose of illustration only and not to limit the scope of the invention in any way, these illustrations follow:

FIG. 2 is a diagram of an image of a specimen mouse realized with the preferred illumination and viewing apparatus in accordance with the present invention previously seen in FIG. 2

FIG. 4, consisting of FIGS. 4a and 4b, are detail illustrations of two different embodiments of a fluorescent calibration step wedge in accordance with the present invention.

DESCRIPTION OF THE PREFERRED EMBODIMENT

The following description is of the best mode presently contemplated for the carrying out of the invention. This description is made for the purpose of illustrating the general principles of the invention, and is not to be taken in a limiting sense. The scope of the invention is best determined by reference to the appended claims.

Although specific embodiments of the invention will now be described with reference to the drawings, it should be understood that such embodiments are by way of example only and are merely illustrative of but a small number of the many possible specific embodiments to which the principles of the invention may be applied. Various changes and modifications obvious to one skilled in the art to which the invention pertains are deemed to be within the spirit, scope and contemplation of the invention as further defined in the appended claims.

In simple terms, the present and related inventions may be considered to be directed to devices, and methods, that serve to replace a simple image, or "snapshot", of a macroscopically-sized specimen—for example a mouse within which multiple dyed bodies separately fluoresce, and where the image essentially shows only that the mouse possesses the (several) dyed bodies—with a sophisticated image where the (i) intensities and (ii) frequencies (colors) of fields appearing within the (composite) image may be precisely known. For example a first tumor of the mouse, seen along a first viewing axis, of size "$Size_A$" may be shown to fluoresce at intensity "$Intensity_A$" and frequency (color) "$Frequency_A$" while a second tumor of the mouse, seen along a separate second viewing axis, may be simultaneously shown in (the composite image) to be of size "$Size_B$" fluorescing at intensity "$Intensity_B$" and at frequency (color) "$Frequency_B$", Still furthermore, these intensities, and frequencies (or wavelengths, or colors) may all be known, and quantified, by comparison to "fluorescence standards" that appear within the same composite images.

1. General Construction, and Function

Figure 1:
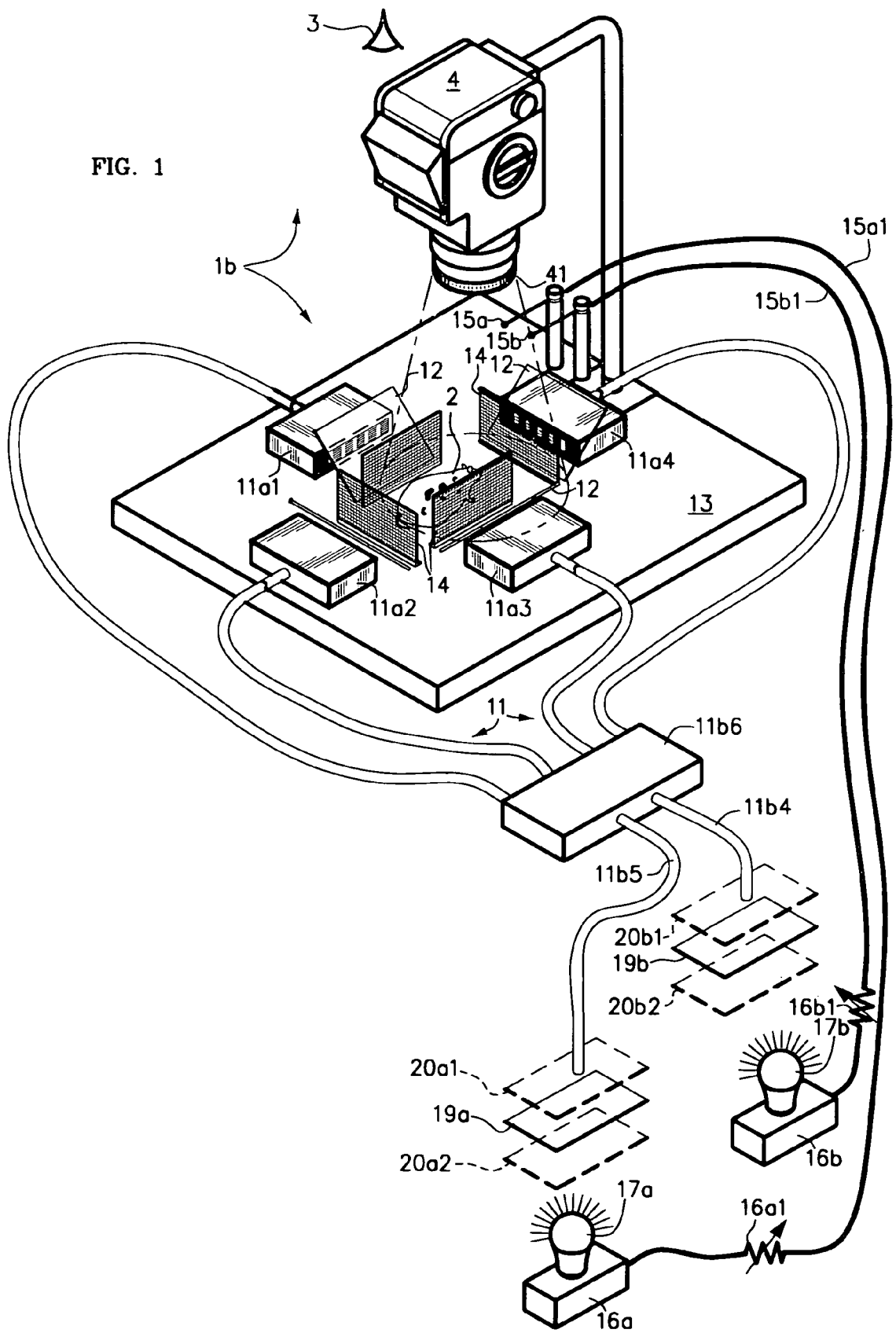
FIG. 1 is a diagrammatic view of an illumination and viewing apparatus in accordance with the present invention.

A diagrammatic view of a first, rudimentary, embodiment of an illumination and viewing apparatus 1 in accordance with the present are related inventions is shown in FIG. 1. Each illumination and viewing apparatus 1 consists of multiple illumination sources 11 illuminating a specimen 2 (not part of the present invention; shown in phantom line) through respective multiple dichroic mirrors 12. In FIG. 1 four such illumination sources 11a1, 11a2, 11a3, 11a4 are illustrated illuminating specimen 2 along four axis.

Thus multiple light beams illuminate specimen 2. The reflections of all such separate light beams as illuminate the specimen 2 from the specimen 2 are, as reflected in the dichroic mirrors 12, simultaneously visible along a viewing axis and to an observer's eyeball 3 or to a camera 4 (neither of which is part of the present invention).

The lens of camera 4 is covered with a bandpass or longpass filter 41, as is conventional. The filter 41 serves to substantially block the illuminating radiation from illumination sources 11—which radiation is otherwise always bright in the image seen by camera 4 (or eyeball 3)—while substantially passing (all) the fluorescent emissions induced by this illumination within specimen 2. For example, if the illuminating radiation was energetic blue light, and the induced fluorescence of both (1) green and (2) red colors, then the bandpass or longpass filter 41 would substantially block blue light, but would pass both green and red light. An optical objective stage, or viewing tube (not shown) may optionally be included.

At least (1) the emitting ends of the multiple illumination sources 11, (2) a cradle (not shown),for the specimen 2 (not part of the present invention), (3) the dichroic mirrors 12, and (4) the optional optical objective stage, or viewing tube (not shown), are held in alignment upon a stage, and by an instrument frame, 13—as is common in the optical instrumentation arts.

The paths of light ultimately appearing in such composite image as appears to the observer's eyeball 3, or to the camera 4, is thus as follows. Light from each of the multiple illumination sources 11 passes in part through an associated one of the dichroic mirrors 12, whereupon a portion of these passed light beams is either (1) are reflected from corresponding regions of the specimen 2, or, more commonly, (2) being absorbed induces fluorescent light emissions from selected areas of the specimen 2. Those portions of the incipient light that are reflected from each respectively illuminated region of the specimen, and/or the induced fluorescent emissions, are substantially reflected in the dichroic mirrors 12 and are directed to the observer's eyeball 3, or the camera 4.

It should also be understood in FIG. 1 that (1) there may be, and commonly is, ambient, or laboratory, lighting, and/or (2) the specimen mouse 2 may also be illuminated from above (illumination source not shown) as required or desired.

Optional filter elements 14 may be any of (1) scales or grid reticules 14a, (2) color filters 14b, and/or (3) fluorescent image calibration step wedges 14c.

In the case of a scale and/or grid reticule element 14, the element may be a clear glass plate or the like marked with a linear, and/or a reticular grid, scale. The grid reticule element 14a may alternatively be in the form of a framed screen or wire grid where parallel and/or intersecting wires or the like span a central aperture bounded by a generally rectangular frame. This scale then appears within the corresponding fields of the composite image, and provides a basis by which the image, and items such as specimen 2 and fluorescent fields appearing therein, may be sized. Notably, this scale can also be impressed upon each or any of the dichroic mirrors 12, in which case no separate scale element 14 needs be included.

The alternative, or additional, element 14 may be in the general nature of a color filter. It may be any of a passband filter of color (i.e., wavelength, or frequency), or a neutral density intensity attenuation filter, or any other type and purpose for which filters are commonly used. A filter element 14 may commonly be inserted within the optical path, as illustrated, in order to preset, or selectively preset, the intensity and/or color and/or color temperature of the composite image or—importantly—selected regions of this image. The composite image regions adjusted by each filter element are, of course, only those regions in which the filter element is within the optical path.

The element 14 may still further be a fluorescent image calibration step wedge, as is the particular subject of the present patent application. Such a fluorescent image calibration step wedge element, discussed in greater detail hereinafter in section 5, is essentially a scale by which any, and most preferably all, of the color properties of color fields appearing within the composite image may be measured. A preferred calibration step wedge element has two color scales, such as might besuit by way of example a green fluorescence and a red fluorescence. By comparison of a portion of the image, such as an image portion of a tumor that is fluorescing green, with an appropriate (green scale) portion of the fluorescent image calibration step wedge element, then the true color, intensity, etc., of this image portion may be rigorously determined.

2. Particular Construction, and Function, to Variably Illuminate with Multiple Colored Illuminating Lights Along Each of Multiple Axis The illumination and viewing apparatus 1 has thus been seen to consist (in part) of multiple illumination sources 11 illuminating a specimen 2 (not part of the present invention; shown in phantom line) through respective ones of multiple dichroic mirrors 12 so as to produce multiple light beams illuminating specimen 2. The reflections of all such separate light beams as illuminate the specimen 2 are, as reflected in the dichroic mirrors 12, simultaneously visible along a viewing axis and to an observer's eyeball 3 or to a camera 4 (neither of which is part of the present invention). An optical objective stage, or viewing tube (not shown) may optionally be included along the viewing axis.

At least (1) the emitting ends 11a–11b of the multiple illumination sources 11, (2) a cradle (not shown) for holding the specimen 2 (not part of the present invention), (3) the dichroic mirrors 12, and (4) the optional optical objective stage or viewing tube (not shown), are held in alignment upon a stage, and by an instrument frame 13—as is common in the optical instrumentation arts.

Particularly in accordance with the present invention, the multi-colored illuminations (2 colors in FIG. 1) along each of the multiple illumination axis (four such axis in FIG. 1), is provided from a reduced number of light sources (2 such light sources 17 in FIG. 1). Moreover, and separately to the innovative provision of the multi-colored lights along each of multiple axis, these lights are separately independently adjustable in intensity.

In accordance with this later aspect of the present invention, one or more sensors of light intensity 15, and/or the intensity of a particular color or fluorescent emission, are located within the path of (fluorescent) light from the specimen 2, in particular between the dichroic mirrors 12, or any and each of them, and the observer's eyeball 3 or camera 4. In FIG. 1 two such sensors 15a, 15b—each of which sensors 15a, 15b senses a particular fluorescent color—are shown. The sensors 15a, 15b of (colored) light intensity 15 are typically held in position upon posts also connected to instrument frame 13, and respectively transmit signals via wires 15a1, 15b1.

The sensors of light intensity 15a, 15b are preferably photoelectric sensors filtered or tuned so as to be sensitive to, most normally, a single expected color (i.e., wavelength, or frequency) of fluorescent emission. Each sensor 15a, 15b intercept(s) emitted fluorescent light over a sufficiently broad area of one optical path so as to detect the (cumulative, aggregate) fluorescent light emissions (if any be present).

The fluorescent emission intensity sensors 15a, 15b operate through wires 15a1, 15a2 and control circuits 16a1, 16b1 of variable power sources 16a, 16b. The control circuits 16a1, 16b1 and variable power sources 16a, 16b are of conventional construction for variably energizing, preferably, incandescent lamps. The incandescent lights are commonly filtered so as to produce the illumination colors of interest by color passband filters 19a, 19b, as is conventional. The variable power sources 16a, 16b in turn power the light sources 17a, 17b. The light sources 17a, 17b are, as stated, preferably incandescent lamps, and are more preferably 150 watt halogen lamps type EKE.

Two such variable power sources 16a, 16b are illustrated respectively powering two light sources 17a, 17b in FIG. 1. The level of each light source 17a, 17b is respectively adjustable by an associated control circuit 16a1, 16b1, each illustrated as a variable resistor. The control circuits 16a1, 16b1 may be on the order of a preset, wherein the general intensity, or level, of the power sources 16a, 16b and associated light source 17a, 17b is adjusted. The control may be on the order of feedback loop, as illustrated in FIG. 1, wherein the intensity of each (fluorescent) color as is detected in the path of optical emissions from specimen 2 is used to adjust the intensity of the very (colored, narrowband) light that will cause the emission of this color.

The light emissions from each of the light sources 17a, 17b is passed through a respective color filter 19a, 19b to be passed through the special, "bifurcated", fiber optic bundle 11 to be emitted at each of the light sources 11a1, 11a2, 11a3, 11a4. Within the optical path, and normally either before or after the color filters 19a, 19b are optionally located one or more optional attenuation 20a1, 20a2 or 20b1, 20b2. These elements 20a1, 20a2, 20b1, 20b2 may be any of (1) neutral density filters, (2) further color filters, and/or, as particularly besuits the construction of the special "bifurcated" fiber optic cable 11, simple mechanical mechanisms that obscure part of the light from a respective light source 17a, 17b to a respective light-receiving, or input, end 11b4, 11b5 of the special "bifurcated" fiber optic cable 11.

This control loop operates to a preset level to brighten the light 17, and the corresponding one light source 11, when the fluorescent emission is dim, and to make less bright the light 17, and the corresponding one light source 11, when the fluorescent emission is bright. Similar illumination light intensity control sensors and paths, not shown, appear on other ones of the illumination paths leading to the light sources 11.

The paths of light ultimately appearing in such composite image as appears to the observer's eyeball 3, or to the camera 4, is thus as follows. Light from each of the multiple illumination sources 11a–11d passes in part through an associated one of the dichroic mirrors 12, whereupon a portion of these passed light beams are reflected, or, more commonly, do induce colored fluorescent emissions from corresponding regions of the specimen 2. Those portion of the incipient light that are reflected from each respectively illuminated region of the specimen and, more commonly, those fluorescent emissions induced in the specimen are reflected in the dichroic mirrors 12 and are directed to the observer's eyeball 3, or the camera 4. Indeed, the dichroic mirrors 12 substantially pass the illuminating radiation, and substantially reflect the induced fluorescent radiation.

3. The Image Formed, and the Filter Elements (Including a Fluorescent Calibration Step Wedge)

Before further detailed exposition of added filter elements 14 including the fluorescent calibration step wedge 14c that is the particular subject of the present invention, a diagram of an image of a specimen mouse realized with the preferred illumination and viewing apparatus 1 in accordance with the present invention may be noted in FIG. 2. The view is clearly "multi-axial", and is in fact along four axis mutually perpendicular by pairs. The view is also panoramic, being 360° around the specimen mouse 2 in one plane and some 180° over the "top" of the mouse in an orthogonal plane.

Figure 3A:
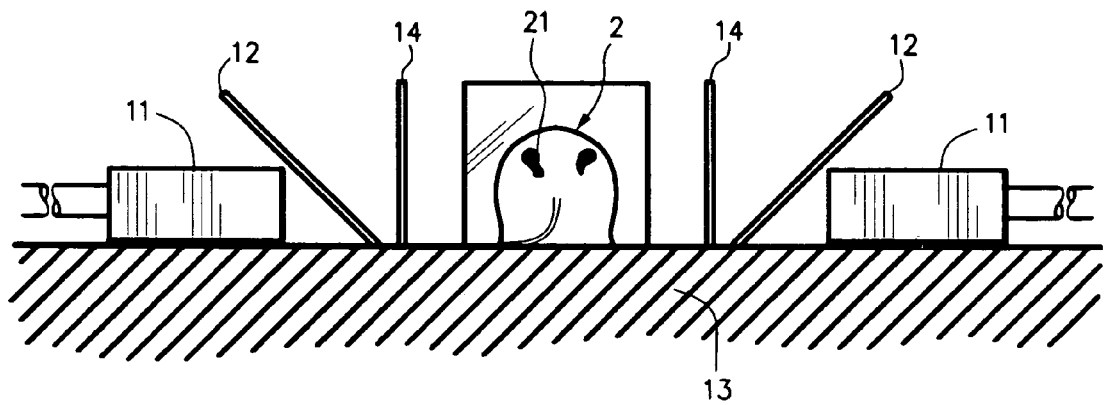
FIG. 3, consisting of FIGS. 3a and 3b, are respective detail side and diagrammatic perspective views of a portion of the preferred illumination and viewing apparatus in accordance with the present invention previously seen in FIG. 1.
Figure 3B:
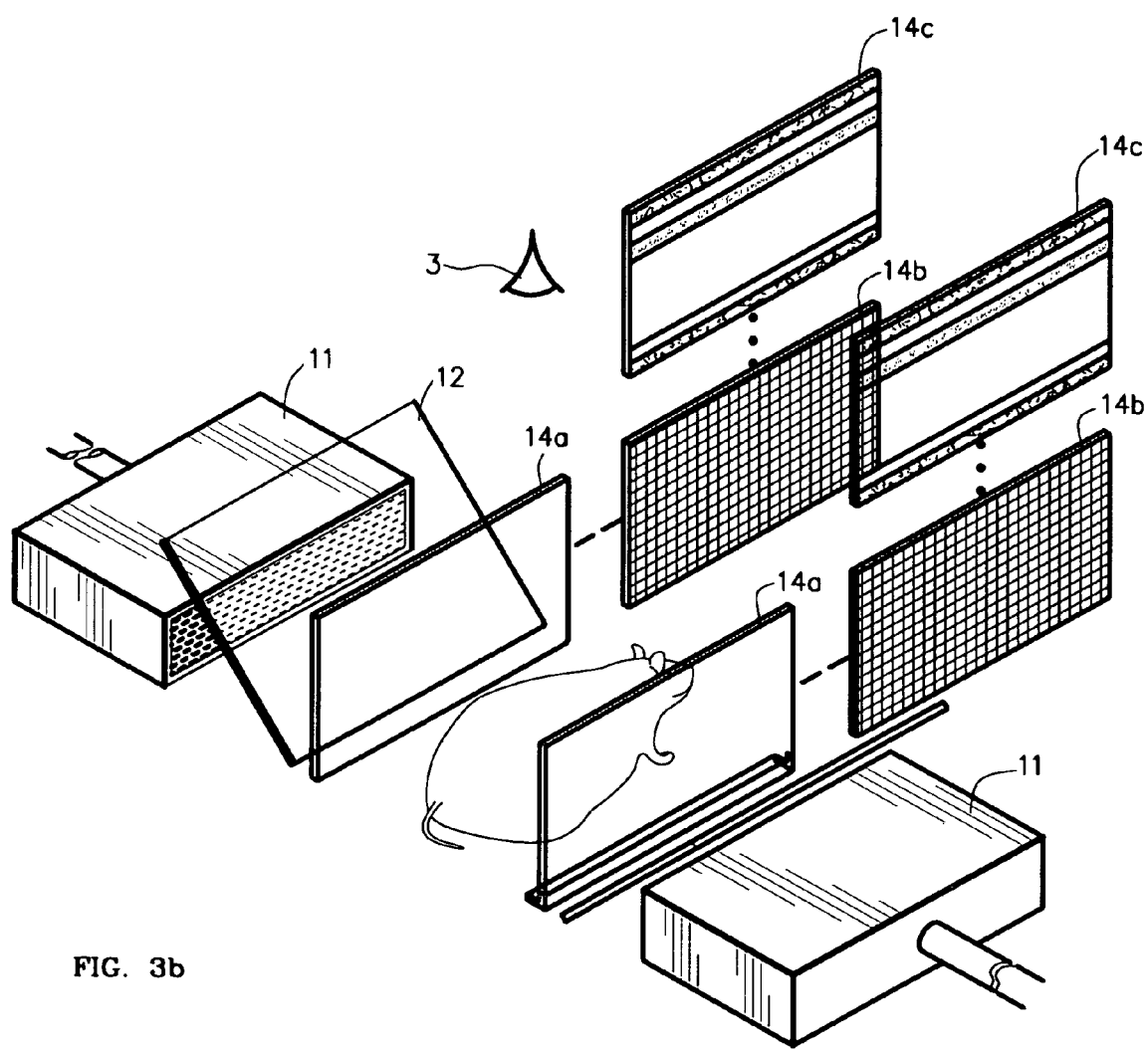

An expansion, and extension, accorded the preferred illumination and viewing apparatus 1 in accordance with the present invention by the addition of filter elements 14 is shown in greater detail in FIG. 3, consisting of FIGS. 3a and 3b. The elements 14 may be noted in both FIG. 1 and in FIG. 3. These elements 14 may be any of (1) scales or grid reticules 14a, (2) color filters 14b, and/or (3) the fluorescent image calibration step wedges 14c (which fluorescent image calibration step wedges 14c are the particular subject of the present invention), all as are best visible in FIG. 3b.

In the case of a scale and/or grid reticule element 14a, the element may be a clear glass plate or the like marked with a linear, and/or a reticular grid, scale. The grid reticule element 14a may alternatively be in the form of a framed screen or wire grid where parallel and/or intersecting wires or the like span a central aperture bounded by a generally rectangular frame. This scale then appears within the corresponding fields of the composite image, and provides a basis by which the image, and items such as specimen. 2 and fluorescent fields 21 appearing therein, may be sized. Notably, this scale can also be impressed upon each or any of the dichroic mirrors 12, in which case no separate scale element 14a needs be included. Still furthermore, any grid scale can be derived from an enclosure (not shown) of the specimen mouse 2.

In the case of a scale and/or grid reticule element 14a, the element is preferably marked with a linear, and/or a reticular grid, scale. This scale then appears within the corresponding fields of the composite image, and provides a basis by which the image, and items such as specimen 2 appearing therein, may be sized. Notably, this scale can also be impressed upon each or any of the dichroic mirrors 12, in which case no separate scale element 14a needs be included.

The alternative, or additional, element 14b is in the general nature of a filter, as is further discussed in the following section 4. It may be any of (1) a passband filter of color (i.e., wavelength, or frequency), or (2) a neutral density intensity attenuation filter, or (3) any other type and purpose for which filters are commonly used. A filter element 14b may commonly be inserted within the optical path, as illustrated, in order to adjust, or selectively adjust, the intensity and/or color and/or color temperature of the composite image (shown in FIG. 2), or—importantly—selected regions of this image. The composite image regions adjusted by each filter element 14b are, of course, only those regions in which the filter element 14b is within the optical path.

The element 14 may still further be a fluorescent image calibration step wedge 14c, as is further discussed in the following section 5. The fluorescent image calibration step wedge 14c is the particular subject of the present invention, although it is suitably used within, and with, the apparatus and methods of the related inventions. The fluorescent image calibration step wedge element 14c is essentially a scale by which any, and most preferably all, of the color properties of color fields appearing within the composite image may be measured. In the illustration of FIG. 3b a fluorescent image calibration step wedge element 14c having two color scales, such as might besuit by way of example a green fluorescence and a red fluorescence, is illustrated. By comparison of a portion of the image, such as a an image portion 21 of a tumor that is fluorescing green, with an appropriate (green scale) portion of the fluorescent image calibration step wedge element 14c, then the true color, intensity, etc., of this image portion may be rigorously determined.

In general the present and related inventions have thus been seen to enable (1) multi-axial, or panoramic, imaging of a macroscopically-sized specimen, (2) automatic, and automatically calibrated, balanced imaging of such specimen, and particularly of multi-colored fields of fluorescent emission from regions of the specimen as such multi-colored fluorescent emissions are induced by illuminating light along each of multiple axis, and even (3) semi-automated positioning of successive specimens for observation and imaging, with photographing of each specimen being automatic.

4. Preferred Embodiments of a "Neutral Density Step Wedge"

The embodiment of element 14 shown in FIG. 1 and as is further shown in greater detail in FIG. 4, consisting of FIGS. 4a and 4b, may be considered to be that embodiment discussed above as the "neutral density step wedge" 14b.

Thus FIG. 4a (or 4b for that matter) may be considered to show a neutral density step wedge 14b—as well as, and alternative, the "fluorescent calibration step wedge" 14c that is the particular subject of the present invention, and that is discussed in the next following section 5. In other words, FIG. 2 illustrates both of two different, and alternative, embodiments of the element 14: both neutral density step wedge 14b and fluorescent calibration step wedge 14c.

In the case of neutral density step wedge 14b, the particular pattern of the cross-hatching within FIGS. 4a, 4b as encodes for color should be ignored, and generally only the difference in the density of the cross-hatching within these FIGS. 4a, 4b should be considered. According to this interpretation, FIG. 4a is the same as FIG. 4b. A neutral density step wedge 14b is preferably based on transparent glass or plastic microscope slides of standard dimensions. It is prepared by coating a slide with a series of metal films of graduated density.

The most preferred process of manufacture is as follows. A clean slide, or a number of slides, are each placed in a metal jig, being a holder of the slide substrate. The jig is machined so that it contains a slot of a size corresponding to the area of coating that is to be deposited during a single evaporation.

The jig and slide are placed in a coating chamber and the chamber is pumped to a high vacuum. A metal alloy, most preferably nickel chrome, is thermally evaporated onto the slides though the slot in the jig until the desired optical density is achieved, the entire process being optically monitored along a path proceeding through the substrate in the region being coated.

The workpiece slide is then removed from the chamber, and re-positioned in the jig so that a portion of the previously-coated area is not masked by the jig. The portion of the substrate still available is subject to a second cycle of evaporation. This results in a second, thicker, film of different optical density, adjacent to the first. This process is continued unit an entire set of slides—now made into a neutral density step wedge 14b—has been created, each slide having adjacent neutral density coatings of desired values. One end region of the slide may be left un-coated for reference purposes.

5. Preferred Embodiments of the "Fluorescent Calibration Step Wedge"

As discussed in section 4 above, the same FIGS. 4a and 4b can also be considered to represent the fluorescent calibration step wedge 14b that is the particular subject of the present invention.

A "green fluorescence" embodiment of the fluorescent calibration step wedge 14c1 shown in FIG. 4a is for calibrating green light fluorescent emissions. It is shown in FIG. 4a encoded by hatching representing the color green, this hatching being relatively more dense where the green light emission is weaker at section 14c1d, and relatively less dense where the green light emission is relatively stronger at section 14c1a.

Likewise, the "red fluorescence" embodiment of the fluorescent calibration step wedge 14c2 shown in FIG. 4b is for calibrating red light fluorescent emissions. This embodiment 14c2 is shown encoded by hatching representing the color red, with this hatching being relatively more dense where the red light emission is relatively weaker at section 14c2d, and relatively less dense where the red light emission is relatively stronger at section 14c2a.

The fluorescent image calibration step wedges 14c1, 14c2 are again preferably based on glass or plastic microscope slides of standard dimensions. This time, however, the glass or plastic microscope slide is not transparent, but rather contains a fluorescent chemical. These slides are again prepared by coating the slide, this time with a stepped series of an appropriate light-obscuring coating, normal nickel chrome, building in graduated steps to greater and greater amounts deposited in successive areas.

The most preferred process of manufacture is as follows. A glass, or a plastic, slide is impregnated during initial formation with a fluorescent chemical concentrate such as is available from the Day-Glow Corporation, USA, in the DAY-GLO-NX product line pigments of that company. Type NX-12 "Rocket Red" may be used for the red-fluorescing slide 14c2, and Phthalo Green may be used for the green-fluorescing slide 14c1. Still other fluorescent colors are possible, such as orange derived from pigments NX-14 "Fire Orange" and/or NX-15 "Blaze Orange"; yellow as derived from pigment NX-17 "Saturn Yellow"; and magenta as derived from pigment MX-21 "Corona Magenta".

The pigment(s) that is (are) within the slide may alternatively be the Skyment pigments available from Zhual Shyhigh Chemicals C. Ltd. 20/F., Everbright International Trade Centre, Zhuhai City, Guangdong Province, PR China.

Still further, the slide may contain quantum dots appropriately sized so as to fluoresce at a desired color.

The clean fluorescent slides are again placed in a metal jig, or holder of the slide substrate. The jig is again machined so that it contains a slot of a width corresponding to the area of chemical coating that is to be deposited during a single evaporation.

The jig and slide are placed in a coating chamber and the chamber is pumped to a high vacuum. A metal, for example and most preferably nickel chrome, is thermally evaporated onto the slides though the slot in the jig until the desired fluorescent emission intensity is achieved, the entire process being optically monitored along a path proceeding through the substrate in the region being coated while the fluorescent chemical is excited to emission by radiation (light) of appropriate properties.

The workpiece slide is then removed from the chamber, and re-positioned in the jig so that a portion of the previously-coated area is not masked by the jig. The portion of the substrate still available is subject to a second cycle of evaporation. This results in a second, thicker, metal film, adjacent to the first, obscuring to a greater degree the fluorescent light emission of the substrate slide. This process is continued unit an entire set of slides and slide regions—now made into fluorescent calibration step wedges—is created, each slide having adjacent regions of fluorescent light emission each at a desired value. In FIGS. 4a and 4b this progression is shown from no coating at regions 14c1a, 14c2a to one coating layer at sections 14c1b, 14c2c progressing to a full three coating layers at sections 14c1d, 142cd. One end region of the slide may be left un-coated with any metal for reference purposes.

Coatings may be put on as is conventional, or may be procured from Chroma Technology Corporation, 10 Imtec Lane, PO Box 489, Rockingham, Vt. 05101 USA. This company will, also provide the plastic slides, but they in turn purchase them from SUNY-Buffalo, Department of Electrical Engineering, Dr. P. C. Cheng, Bonner Hall, Buffalo, N.Y. 14260. Additional sources of fluorescent plastic slides and dyes would be Day-Glo and Skyment pigments. A user may make his or own slide, particularly from liquid polymer plastic, by the simple expedient of mixing fluorescent pigment in a liquid, and then letting the liquid and contained pigment harden within a mold in shape of a slide, until the desired fluorescent light emission is (with appropriate stimulation) achieved.

7. Practice of the Present and Related Inventions

The present and related inventions have thus been seen to be embodied in a calibrated apparatus for illuminating along multiple viewing axis a macroscopically-sized specimen for observation along a single viewing axis. The illuminating radiations may be of multiple intensity, and multiple colors (i.e., wavelengths, or frequencies).

The most preferred apparatus includes a stage for supporting a specimen to be observed, at least one first illumination source of first radiation of some first intensity and color (i.e., wavelength, or frequency), and at least one second illumination source of second radiation that differ differs from the first radiation in intensity, in color (i.e., wavelength, or frequency), or in both intensity and color. A special fiber optic cable receives the first radiation into a first one of two radiation-receiving, or input, ends and receives the second radiation into a second one of the two radiation-receiving ends. Optionally even more than two radiations can be received, and combined, by the principles of the present invention.

This same special fiber optic cable produces at each of at least two radiation-emitting, or output, ends both the first radiation and the second radiation. This combined, dual-frequency (or even multiple-frequency) radiation is used to illuminate the specimen supported upon the stage along at least two separate illumination, and viewing, axis.

The fiber optic cable preferably consists of (1) a first large number of fiber optic strands receiving the first radiation at the first one of the two radiation-receiving, or input, ends and (2) a second large number of fiber optic strands receiving the second radiation at the second one of the two radiation-receiving, or input, ends. Normally the first and second large numbers are equal, but they need not be, and may be, by way of example, in a predetermined ratio such as 2:3.

The first large number of fiber optic strands is substantially interspersed with the second large number of fiber optic strands within the special fiber optic cable, and vice versa. Moreover, an approximately equal number of total fiber optic strands are routed to each of the at least two radiation-emitting, or output, ends.

Thus, due to the interspersing of the fiber optic strands, the radiation output at each of the at least two radiation-emitting, or output, ends is a combination, normally an equal combination (at least in area of emission), of the first radiation and the second radiation. Moreover, this output of both the first and the second radiation at each of the at least two radiation-emitting, or output, ends is substantially the same (i.e, within 10%). Still further, the output of both the first and the second radiation between all of the at least two radiation-emitting, or output, ends is substantially the same (i.e., within 10%).

The multi-axis specimen illumination and viewing apparatus so constructed is particularly preferred for use in observing a specimen that is fluorescent in selective regions responsive to both the first radiation and the second radiation. So used the apparatus preferably further includes a dichroic mirror located between the each output end of the special "bifurcated" fiber optic cable and the specimen. By this arrangement at least some emission of fluorescent radiation induced in the specimen by each of the first radiation and the second radiation will be reflected by the dichroic mirror into an optical path that includes the viewing axis.

The multi-axis specimen illumination and viewing apparatus preferably includes a first source of radiation of a first color (i.e., at a first wavelength, and frequency) (at a first intensity), and a second source of radiation of a second color (i.e., at a second wavelength, and frequency) (at a second intensity). The first illumination source may consist of a first passband filter located between a source of radiation and the first one of the two bifurcated ends of the bifurcated fiber optic cable. This first passband filter passes radiation of the first color (i.e., wavelength, or frequency) from the source of radiation into the first one of the two radiation-receiving, or input, ends of the special "bifurcated" fiber optic cable. Likewise, the second illumination source may consist of a second passband filter, now located between the source of radiation and the second one of the two radiation-receiving, or input, ends of the special "bifurcated" fiber optic cable. This second passband filter passes radiation of a second color (i.e., a second wavelength, or second frequency) from the source of radiation into the second one of the two radiation-receiving, or input, ends of the special "bifurcated" fiber optic cable.

Alternatively, or additionally, the source of radiation may be coupled with a neutral density filter located between a common source of radiation and either, or both, of the two radiation-receiving, or input, ends of the special "bifurcated" fiber optic cable.

Alternatively, an aperture filter may be located between the source of radiation and either, or both, or the two radiation-receiving, or input, ends of the special "bifurcated" fiber optic cable. Uniquely, due to the special construction of fiber optic cable, this aperture filter may be simply a selectively occludable aperture within a frame, much in the manner of a sliding window, or door. The selectively occludable aperture passes relatively more radiation from an illumination source to an associated radiation-emitting, or output, end of the special "bifurcated" fiber optic cable when the aperture is opened, and relatively less radiation from an illumination source to the associated output end of the special "bifurcated" fiber optic cable when the aperture is closed.

Additionally, the present invention is embodied in a method for illuminating a macroscopically-sized specimen for observation along a viewing axis with radiation of multiple colors (i.e., wavelengths, or frequencies).

In the preferred method a macroscopically-sized specimen is illuminated for observation along a viewing axis by (1) supporting upon stage a specimen to be observed, (2) first illuminating with first radiation of a first frequency a first one of two radiation-receiving, or input, ends of a special "bifurcated" fiber optic cable, and (3) second illuminating with second radiation of a second color (i.e., wavelength, or frequency), different than the first frequency, a second one of two radiation-receiving, or input, ends of the special "bifurcated" fiber optic cable, meanwhile to (4) third illuminating with both first-frequency first radiation, and also second-frequency second radiation, the specimen supported upon the stage from each of multiple radiation-emitting, or output, ends of special "bifurcated" cable, each radiation-emitting, or output, end of special "bifurcated" cable illuminating the specimen along a separate the viewing axis.

This method may in particular be applied to illuminating a specimen that is fluorescent in each of multiple colors to so as to cause the specimen to emit various, and variously colored, radiations from various selective regions. Normally induced fluorescent emissions at a first color are responsive to the first radiation, and induced fluorescent emissions at a second color are responsive to the second radiation. If an emission of any color is desired to be accentuated, or enhanced, then the intensity (or, more rarely, the color) of the associated illuminating radiation is increased (or, more rarely, made to be of a color that is more productive of the associated fluorescence). Conversely, if an emission of any color is desired to be attenuated, or diminished, then the intensity (or, more rarely, the color) of the associated illuminating radiation is decreased (or, more rarely, made to be of a color that is less productive of the associated fluorescence).

The ability to modify the relative, and regional, and axial, intensity of fluorescent emissions from the specimen, including automatically so modifying, by act of modifying the corresponding intensities and/or color of the associated relative, and regional, and axial, illuminating radiations is an important aspect of the present and related inventions.

The method preferably further includes reflecting with a dichroic mirror, located between the single end of the bifurcated fiber optic cable and the specimen, at least some of the colored fluorescent radiations that are emitted by the specimen (responsively to each of the first radiation and the second radiation) into an optical path that includes the viewing axis.

In one variant preferred method the first illuminating with first radiation of a first frequency the first one of two radiation-receiving, or input, ends of a special "bifurcated" fiber optic cable consists of: (1) producing radiation including radiation of the first and the second frequencies in a radiation source, and (2) filtering with a first passband filter, located between the radiation source and a first one of two radiation-receiving, or input, ends of a special "bifurcated" fiber optic cable, radiation received from the radiation source so that radiation of the first frequency is passed into this first one of the two radiation-receiving, or input, ends of the special bifurcated fiber optic cable. Likewise, the second illuminating with second radiation of a second frequency the second one of two radiation-receiving, or input, ends of the special "bifurcated" fiber optic cable then consists of filtering with a second passband filter, located between the radiation source and the second one of the two radiation-receiving, or input, ends of the special "bifurcated" fiber optic cable, radiation from the radiation source so that radiation of the second frequency is passed into this second one of the two radiation-receiving, or input, ends of the special "bifurcated" fiber optic cable.

Either, or both, of the first illuminating with first radiation of a first frequency the first one of two radiation-receiving, or input, ends of a special "bifurcated" fiber optic cable, and the second illuminating with second radiation of a second frequency of the second one of two radiation-receiving, or input, ends of the same special "bifurcated" fiber optic cable, may include, or also, include filtering with a neutral density filter radiation that is passed into the either, or both, radiation-receiving, or input, ends of the same special "bifurcated" fiber optic cable.

Either, or both, of the first illuminating with first radiation of a first frequency the first one of the two radiation-receiving, or input, ends of the special "bifurcated" fiber optic cable, and the second illuminating with second radiation of a second frequency the second one of the two radiation-receiving, or input, ends of the same special "bifurcated" fiber optic cable, may include filtering with an aperture filter radiation that is passed into the an associated one of the two radiation-receiving, or input, ends of the same special "bifurcated" fiber optic cable.

If the filtering is with an aperture filter, it is preferably so with an aperture filter serving to selectively occlude with a variable size aperture within a plate radiation passing to the associated radiation-receiving, or input, end of the special "bifurcated" fiber optic cable so that relatively more radiation passes to the associated ends of the special "bifurcated" fiber optic cable when this aperture is opened, and so that relatively less radiation passes to the associated radiation-emitting, or output, ends of the special "bifurcated" fiber optic cable when this aperture is closed.

Finally, all such fluorescent emissions as are produced within a composite image may be compared with the various, stepped, intensities of a fluorescent calibration step wedge subject to the exact same illumination as was the specimen, and appearing in the same composite image at the same time.

9. Conclusion

In the most preferred embodiment of the present and related inventions multi-color (or dual color) (i.e., multi-frequency, or multi-wavelength) illumination is preferably realized along each of four illumination axis (specimen left, right, front and rear as is shown in FIG. 1b) by two only lamps each of which can have its light output adjusted. The light output is commonly so adjusted by changing the (d.c.) voltage to the lamp with the light output of the lamp being proportionately changed. The light output of each lamp is then preferably projected through one or more associated color, or neutral density, filters are within optical paths leading into each of two ends of a special "bifurcated" fiber optic cable. The light outputs of two lamps—which lamps are most commonly at different intensities and also different colors (i.e., wavelengths, or frequencies) and the light in each path from each lamp which may be filtered—is thus distributed, normally equally, to, ultimately, four separate cable ends, as illustrated in FIG. 1. Use of the special "bifurcated" fiber optic cable permits of independently adjustment of the light intensity in each illumination path, and between illumination paths. Moreover, the economies of illuminating light production and distribution within the apparatus are much improved.

The fluorescent calibration step wedges, or calibrated emitters of colored fluorescent lights, of the present invention are preferably abundantly used in all optical, and imaging, paths. These calibration elements appear within the final composite image, and in portions of it. There so appearing, they serve to permit calibration of the intensity (ies), and also the color(s), of all those fluorescing regions of the specimen that also receive the same illuminating radiation (light). Different illuminating radiations along different, and along the same, illumination axis regionally induce the fluorescing of both (1) selected features of the specimen and (2) the calibration element.

In accordance with the preceding explanation, variations and adaptations of the apparatus and method for illuminating and panoramically viewing a macroscopically-sized specimen along a single axis at a single time in accordance with the present invention will suggest themselves to a practitioner of the optical arts.

For example, the dichroic mirrors 12 need not be made straight, in segments to surround specimen 2, but rather one single dichroic mirror 12 in shape of a shallow bowl could be made an used to support continuous panoramic illumination and viewing.

For example, the (1) intensity and (2) color calibration functions of the fluorescent calibration step wedges can be split, or combined, between one or more physical bodies.

In accordance with these and other possible variations and adaptations of the present invention, the scope of the invention should be determined in accordance with the following claims, only, and not solely in accordance with that embodiment within which the invention has been taught.

What is claimed is:

1. An element for calibrating fluorescent light emissions comprising:

a body having a plurality of regions suitably simultaneously to induce fluorescence so as to fluoresce at a corresponding plurality of fluorescent light emission intensities, certain regions appearing to fluoresce relatively more brightly while other regions appear to fluoresce relatively less brightly;

wherein when the body is illuminated and imaged in a same image field and along with a macroscopic specimen also exhibiting fluorescence at multiple areas and intensities then the body serves as an image calibration step wedge, or gauge, where any of intensities, colors, dimension, overall brightness, and color temperature of any and all of the multiple specimen fluorescent areas may be determined to be properly so imaged, meaning that the each and all specimen areas are imaged so as to show other than black, or no image, but less than saturation;

wherein, by comparison to the body that is within a same image, illumination of the specimen may be adjusted so that the full range of all its fluorescent emissions, dim to bright, are captured within a single image.

2. The fluorescent light emissions calibration element according to claim 1 wherein the body comprises:

a substantially planar substrate; and at least one fluorescent substance within the substrate; and one or more coatings applied to different effect in the plurality of areas of the substrate so that the different ones of these plurality of substrate regions will, upon exposure to radiation sufficient to induce fluorescent emissions of the fluorescent substance, appear to fluoresce relatively more brightly while other regions will appear to fluoresce relatively less brightly.

3. The fluorescent light emissions calibration element according to claim 2 wherein the same coating is applied at various thickness to different ones of the plurality of areas of the fluorescent-substance-containing substrate so that relatively less thickly coated regions of the fluorescent-substance-containing substrate will, upon exposure to radiation sufficient to induce fluorescent emissions of the fluorescent substance, appear to fluoresce relatively more brightly while relatively more thickly coated regions of the fluorescent-substance-containing substrate will, upon exposure to the same radiation sufficient to induce fluorescent emissions of the fluorescent substance, appear to fluoresce relatively less brightly.

4. The fluorescent light emissions calibration element according to claim 2 wherein the substantially planar substrate comprises:

glass.

5. The fluorescent light emissions calibration element according to claim 2 wherein the substantially planar substrate comprises:

plastic.

6. The fluorescent light emissions calibration element according to claim 2 wherein the fluorescent substance comprises:

a fluorescent chemical.

7. The fluorescent light emissions calibration element according to claim 2 wherein the fluorescent substance comprises:

quantum dots.

8. The fluorescent light emissions calibration element according to claim 2 wherein at least one coating comprises:

nickel chrome.

9. The fluorescent light emissions calibration element according to claim 2 wherein at least one coating is so applied in various regions to the substrate at the variable extent by dint of being applied to the substrate in multiple regions at a first time, and to be re-applied to less than all of the multiple regions upon at least one more, second, time;

wherein the at least one coating is more abundant in those of the multiple regions whereat it has been applied at least two times than any regions whereat it has been applied but one time.

10. The fluorescent light emissions calibration element according to claim 9 wherein the at least one coating is so applied in various regions to the substrate at the variable extent by dint of being applied and re-applied to the substrate in each of multiple regions for a variable number of times;

wherein accumulations of the coating will be greatest in those regions of the substrate whereat the coating has been applied multiple times.

11. An apparatus for illuminating a macroscopically-sized specimen for observation along a viewing axis, the apparatus comprising:

a stage for supporting a specimen to be observed; a first illumination source of first radiation of a first color; a second illumination source of second radiation of a second color, different from the first color;

an element for calibrating fluorescent light emissions induced by each of the first and the second radiations, the element having a body having a plurality of regions that fluoresce under illumination to a corresponding plurality of fluorescent light emission intensities, certain regions appearing to fluoresce relatively more brightly while other regions appear to fluoresce relatively less brightly.

12. The apparatus according to claim 11 further comprising:

a first sensor sensing induced fluorescent radiation emission from a region of the element that is responsive to the first radiation to fluoresce so as to produce a first signal; and a first control circuit, responsive to the first signal, for controlling the first radiation output of the radiation source so that this radiation output is relatively greater when the induced fluorescent radiation emission of the element is sensed by the first sensor to be relatively less, and is relatively lesser when the induced fluorescent radiation emission of element is sensed by the first sensor to be greater.

13. The apparatus according to claim 12 further comprising:

a second sensor sensing induced fluorescent radiation emission from a region of the element that is responsive to the second radiation to fluoresce so as to produce a second signal; and a second control circuit, responsive to the second signal, for controlling the second radiation output of the radiation source so that this radiation output is relatively greater when the induced fluorescent radiation emission of the element is sensed by the second sensor to be relatively less, and is relatively lesser when the induced fluorescent radiation emission of element is sensed by the second sensor to be relatively greater.

* * * * *